(12) United States Patent
Wulf et al.

(10) Patent No.: US 7,371,347 B2
(45) Date of Patent: May 13, 2008

(54) DEVICE FOR DISPENSING AND OBSERVING THE LUMINESCENCE OF INDIVIDUAL SPECIMENS IN MULTI-SPECIMEN ARRANGEMENTS

(75) Inventors: Juergen Wulf, Ueberlingen (DE); Werner Pongratz, Fronreute (DE); Andreas Fina, Ueberlingen (DE); Michael Heil, Uhldingen-Meuhlhofen (DE); Michael Jurtz, Ueberlingen (DE)

(73) Assignee: CyBio AG, Jena (DE)

( * ) Notice: Subject to any disclaimer, the term of this patent is extended or adjusted under 35 U.S.C. 154(b) by 133 days.

(21) Appl. No.: 10/630,199

(22) Filed: Jul. 30, 2003

(65) Prior Publication Data

US 2004/0022689 A1 Feb. 5, 2004

(30) Foreign Application Priority Data

Aug. 2, 2002 (DE) .............................. 102 36 029

(51) Int. Cl.
*B01L 3/02* (2006.01)
(52) U.S. Cl. ........................................ 422/100; 422/65
(58) Field of Classification Search ................ 422/100, 422/65
See application file for complete search history.

(56) References Cited

U.S. PATENT DOCUMENTS

| 4,366,118 | A | 12/1982 | Bunce et al. |
| 4,431,307 | A | 2/1984 | Suovaniemi |
| 4,684,250 | A | 8/1987 | Kukka et al. |
| 4,735,778 | A | 4/1988 | Maruyama et al. |
| 4,772,453 | A | 9/1988 | Lisenbee |
| 4,828,386 | A | 5/1989 | Matkovich et al. |

(Continued)

FOREIGN PATENT DOCUMENTS

DE 199 11 456 9/2000

(Continued)

*Primary Examiner*—Jill Warden
*Assistant Examiner*—Natalia Levkovich
(74) *Attorney, Agent, or Firm*—Reed Smith LLP (57) ABSTRACT

The invention is directed to a device for dispensing and observing the luminescence of individual specimens in multi-specimen arrangements, particularly for the examination of biological, chemical or cytobiological assays with high specimen throughput. It is the object of the invention to find a novel possibility for dispensing in multi-specimen arrangements (microplates) and for observing the luminescence of the individual specimens, particularly for examining biological assays with high specimen throughput, which permits an immediate observation of the course of luminescence while dispensing proceeds at the same time without being limited to a determined type of microplate. This object is met, according to the invention, in that the dispensing unit has at least one linear dispensing comb containing an even number of dispensing nozzles representing an integral divisor of the number of wells along one dimension of the microplate, the dispensing combs are arranged so as to be displaceable orthogonal to their longitudinal dimension, every dispensing comb is connected to a controllable pump for metering the amount of liquid to be dispensed without immersion in the wells of the microplate, and the CCD camera is oriented by a fast optical system to a large-area rectangular region of the underside of the microplate across from the dispensing unit, the surface being adapted to the dimension of the dispensing comb and to the area of the microplate covered by the dispensing comb, so that the elapsed time for the luminescence is measurable simultaneously while dispensing continues.

25 Claims, 8 Drawing Sheets

U.S. PATENT DOCUMENTS

| | | |
|---|---|---|
| 4,956,150 A | 9/1990 | Henry |
| 5,306,510 A | 4/1994 | Meltzer |
| 5,828,498 A * | 10/1998 | Sekiya et al. ............... 359/660 |
| 6,372,185 B1 | 4/2002 | Shumate et al. |
| 6,506,611 B2 | 1/2003 | Bienert et al. |
| 6,558,623 B1 * | 5/2003 | Ganz et al. ................... 422/63 |
| 6,584,052 B1 * | 6/2003 | Phillips et al. ........... 369/53.28 |
| 6,731,845 B1 * | 5/2004 | Gerdt ......................... 385/116 |
| 2001/0048899 A1 * | 12/2001 | Marouiss et al. .......... 422/100 |
| 2002/0176801 A1 * | 11/2002 | Giebeler et al. ......... 422/82.05 |
| 2003/0230521 A1 * | 12/2003 | Schick ....................... 210/110 |
| 2004/0022677 A1 * | 2/2004 | Wohlstadter et al. ......... 422/52 |

FOREIGN PATENT DOCUMENTS

| | | |
|---|---|---|
| EP | 0 025 350 | 3/1981 |
| EP | 0 753 734 | 1/1997 |
| WO | WO 01/07896 | 2/2001 |

* cited by examiner

DEVICE FOR DISPENSING AND OBSERVING THE LUMINESCENCE OF INDIVIDUAL SPECIMENS IN MULTI-SPECIMEN ARRANGEMENTS

CROSS-REFERENCE TO RELATED APPLICATION

This application claims priority of German Application No. 102 36 029.4, filed Aug. 2, 2002 the complete disclosure of which is hereby incorporated by reference.

BACKGROUND OF THE INVENTION a) Field of the Invention

The invention is directed to a device for dispensing and for observing the luminescence of individual specimens in multi-specimen arrangements, particularly for the examination of biological, chemical or cytobiological assays with high specimen throughput (HTS and UHTS). It is suitable in particular for the observation of short-term luminescence phenomena (flash luminescence) directly after dispensing into a plurality of cavities or wells of microtitration plates (microplates) of the type mentioned above.

b) Description of the Related Art

It is particularly important in biochemistry and pharmacology to test as many different substances as possible in the microtitration plates (microplates) within a short period of time by adding reagents or cells. This is usually carried out in the form of an assay in which it is precisely determined at what time the microplate with its specimens must be at what location in what sequence. Usually, the reactions of living cells on substances of pharmacological interest are tested. For this purpose, the cells must be kept in a nutrient medium at a specified temperature and mixed with substances, kept in the incubator again for a defined period of time, etc. But the reverse is also possible, namely, the addition of substances to the wells of the microplate which are charged with reagents or cells.

In many cases, this preparatory handling concludes with the optical measurement of luminescence. For this purpose, one or more reagents are added to the cells before or at the moment of measuring the light. Liquid is added to as many (or all) of the wells of the microplate as possible and, further, the light emission is measured simultaneously starting with the addition of liquid. In this connection, there are many competing demands when high plate throughput is to be achieved with automatic HTS (High Throughput Screening) or UHTS (Ultra-High Throughput Screening).

Since the generated light signals are sometimes expected over only a few seconds, a measurement of intensity with a time resolution in the range of seconds per well is required. However, the total measurement time over an entire microplate should be short.

Due to the high cost of the complex compounds of the dispensing reagents, only a few microliters of a diluted solution may be used on the specimen. This means that a highly sensitive detection system is required (possibly photon counters, e.g., SEV or PMT); conventional video camera systems are not sufficiently sensitive for this purpose.

The reproducible addition of defined amounts of liquid is commonly carried out simultaneously by means of pipetting devices which must be rinsed in the interim in a rinsing station after every pipetting step in order to prevent spreading or entrainment of specimens as a result of immersion in the specimen liquid of the wells. Consequently, all wells of a microplate are pipetted simultaneously for high microplate throughput. This requirement limits the applicability of the device to different types of microplates or requires considerable extra expenditure for changing the pipetting heads.

While a recently introduced contactless method for dispensing (DE 199 11 456 A1) does away with the intermediate rinsing of the dispensing head, it is only applicable to a limited number of dispensing nozzles because of a defined pump control, so that the dispensing head must be displaced by steps relative to the microplate in such a way that the dispensing process can not be accomplished in one step for the entire microplate and the dispensing process is therefore prolonged.

Numerous pipetting devices or dispensing devices are known from the prior art which have an optical observation device for measuring luminescence phenomena resulting from the addition of a reagent in order to be able to detect determined ingredients in the wells of the microplate.

For example, U.S. Pat. No. 4,772,453 describes a device which permits the measurement of luminescence in microplates in that a liquid is added at a fixed time prior to measurement and the measurement is carried out sequentially well by well by means of a photomultiplier (SEV or PMT). The microplate is moved by means of an x-y table. Liquid is injected into the next well to be measured in parallel with the measurement that is taking place.

A disadvantage consists in the large expenditure of time for measurement and in the fact that no simultaneity is achieved between the addition of liquid and the measurement, i.e., an immediate brief light reaction, or flash luminescence as it is called, can not be tracked.

The solution in U.S. Pat. No. 4,366,118 is similarly conceived. This patent likewise describes a sequential readout by PMT. In this case, the addition of substances for light reaction is carried out directly over the measuring position, i.e., simultaneous with the measurement. As in U.S. Pat. No. 4,772,453, the disadvantage consists in the large amount of time spent for measuring well by well in the same way when measuring times in the range of seconds are required.

The European Patent Application EP 0 025 350 describes a luminescence apparatus which allows simultaneous dispensing and measurement. The dispenser comprises a quantity of injection tubes which are moved along with a detector located under every tube in the manner of a fork suspension.

This is disadvantageous in that the detectors must remain below the cups in order to be able to track the time elapsed during a short luminescence phenomenon after dispensing in the wells. It is possible to move to the next column of the microplate only when the measurement has been concluded, i.e., the measurement of a microplate takes a very long time because it is possible to dispense in and measure only one column of the microplate at a time.

WO 01/07896 discloses an apparatus which reads out the luminescence from a microplate from above by means of a cooled CCD camera. Consequently, the addition of liquid is carried out outside the measurement chamber prior to measurement. Further, the optics employ a special Fresnel lens for imaging. The cooled CCD camera which requires long integration times for detecting corresponding intensities of luminescence seems disadvantageous in this case. Individual photons can not be detected. Further, since the camera does not measure at the same time that liquid is added, flash luminescence processes taking place within a few seconds and any fast kinetics over the course of the luminescence can not be recorded.

EP 0 753 734 discloses a device for measuring luminescence accompanied by the addition of liquids. In this case, two different reagents are added in succession with different stationary dispensing units, the microplate being moved below them. Optics for transferring the luminescent light to a video camera are arranged below the microplate in the position of the second dispensing unit. This is disadvantageous in that the first stationary dispensing unit can only be used for adding reagents without luminescence or with luminescence that is not time-critical because the addition of liquid is carried out outside of the measuring area of the camera. Accordingly, the device is only suitable for certain reaction processes. Moreover, (as in EP 0 025 350) measuring and dispensing can not be carried out simultaneously. However, this is not provided probably because the dispensing device has an integrated washing station in which the dispensing tips are rinsed during the ongoing measurement due to the immersion in the liquids of the wells for preventing entrainment of specimens. However, this likewise limits the specimen throughput of an HTS regime.

OBJECT AND SUMMARY OF THE INTENTION

It is the primary object of the invention to find a novel possibility for dispensing in multi-specimen arrangements (microplates) and for observing the luminescence of the individual specimens, particularly for examining biological, chemical or cytobiological assays with high specimen throughput (HTS) which permits an immediate observation of the course of luminescence while dispensing proceeds at the same time without being limited to a determined type of microplate.

According to the invention, in a device for dispensing and observing the luminescence of individual specimens in multi-specimen arrangements, particularly for the examination of biological, chemical or cytobiological assays with high specimen throughput (HTS), containing a microplate with a plurality of wells arranged in rows and columns, a dispensing unit with a fixed quantity of dispensing tips which is arranged over the microplate, a table system for moving the microplate relative to the dispensing unit, an optical system by which luminescent light that is excited in the wells of the microplate due to the dispensing is transmitted to a CCD camera, wherein the optical system and the CCD camera are arranged below the microplate and all of the above-mentioned components are located in a light-tight housing, the above-stated object is met in that the dispensing unit has at least one linear dispensing cam or comb having a symmetric treelike structure, this dispensing comb containing an even number of dispensing nozzles representing an integral divisor of the number of wells along one dimension of the microplate, in that the dispensing combs are arranged so as to be displaceable orthogonal to their longitudinal dimension in order to dispense successively in a preselected area, in that every dispensing comb is connected to a controllable pump for metering the amount of liquid to be dispensed in order to dispense without immersion in the wells of the microplate, and in that the CCD camera is oriented by means of the optical system to a large-area rectangular region of the underside of the microplate across from the dispensing unit, the surface in one dimension being adapted to the longitudinal dimension of the dispensing comb and in the other dimension to the area of the microplate covered by the displacement of the dispensing comb, so that the elapsed time for the luminescence is measurable simultaneous with the ongoing dispensing in each of the columns of wells of the microplate in which dispensing is carried out successively.

The quantity of nozzles of a dispensing comb is advantageously equal to the quantity of wells in the columns of the microplate, so that the comb needs to be displaced continuously relative to the microplate exclusively in a direction orthogonal to the longitudinal dimension of the comb.

In order to increase the flexibility for dispensing in different microplates, the selected quantity of nozzles of the dispensing comb is advisably less than the quantity of wells of the columns of the microplate such that the quantity of wells in the columns of the microplate is an integral multiple of the quantity of dispensing nozzles of the comb, and after the column-wise displacement of the dispensing comb transverse to its longitudinal dimension (in x-direction) the microplate is displaceable in longitudinal direction of the comb (y-direction) by a number of row spaces equal to the quantity of nozzles of the dispensing comb so that the displacement of the dispensing comb can then be repeated in the x-direction.

It has proven advantageous when the dispensing unit has a plurality of dispensing combs which are arranged parallel to one another, rigidly coupled with one another and arranged so as to be displaceable over the surface of the microplate observed by the CCD camera.

Accordingly, the dispensing combs can advisably be used for successively dispensing different substances in the same wells of the microplate. Further, it can be advantageous that the dispensing unit has, in addition, controllable valves for each dispensing comb for switching between different dispensing substances, and the valves are arranged in front of the pump of every comb. This further increases flexibility for adding different reagents to the specimens of one microplate or different microplates during operation. For this purpose, a waste trough is provided next to the microplate and the used liquid contents can be emptied out of the comb, pump and connection tubes into the waste trough after switching the valve.

In another arrangement of the dispensing unit with a plurality of coupled dispensing combs, the dispensing combs are advantageously provided for successively dispensing one and the same substance in different wells of the microplate.

Also, it is advisable to use a plurality of dispensing combs when the distance between the nozzles of a dispensing comb is a multiple of the distance between the wells of the microplate. This is the case, for example, when using combs with a distance of 4.5 mm between the nozzles for a 1536-well microplate (with a well spacing of 2.25 mm). In this case, the first comb can only dispense in the odd-numbered wells and a second comb can dispense only in the even-numbered wells in the columns of the microplate. The dispensing combs used for the 96-well and 384-well microplates can therefore also be used for the currently largest standard microplates (with 1536 wells) in that the two dispensing combs are arranged so as to be offset parallel to one another by half of the distance between nozzles.

However, a larger distance between nozzles of the dispensing comb can also be adapted to a more compact grid of microplate wells in another manner. For this purpose, only one dispensing comb is advisably arranged in such a way that it is displaceable along its longitudinal dimension relative to the microplate by half of the distance between the nozzles of the comb.

The relative displacement of the dispensing comb by a fraction of the nozzle distance can advantageously be carried out on the one hand by displacing the microplate in the y-direction between two or more different positions by means of the table system and, on the other hand, by displacing the dispensing unit between two or more different positions in y-direction without changing the position of the microplate, wherein the continuous displacement of the comb in x-direction is carried out between the displacement steps in y-direction for dispensing in and simultaneously observing the rows of microplate wells.

For optical measurement of weak luminescent light, the optical system of the CCD camera advisably has an objective of high light gathering capacity, or fast objective, an electron-optical light intensifier, and reducing relay optics. However, with a cooled CCD camera, the light intensifier could also be dispensed with as the case may be.

A commercial objective which images the microplate completely on the chip of the CCD camera can advantageously be used as a fast objective of the optical system.

In a particularly advantageous manner, a telecentric objective with a high numerical aperture is provided as fast optical system by which preferably a rectangular section of the microplate (known as a tile) can be imaged on the chip of the CCD camera, and the dispensing unit is arranged above the visual field of the CCD camera that is defined in this way and its displacing area is adapted to the available visual field of the CCD camera. In so doing, the microplate is preferably divided into eight rectangular portions (tiles) of the same size which can be introduced one after the other into the visual field of the CCD camera continuously and without overlapping by means of the x-y table system. The longer edge of the chip of the CCD camera is oriented in the direction of the short side of the microplate in order to compensate extensively for the linear magnification or side ratios between the CCD and the tile of the microplate and in order to make use of the whole visual field of the CCD camera.

In order to adapt to different types of microplates, it is advantageous to provide an adapter holder for fastening to the table system in order to ensure a constant height of the upper surface of the microplate under examination in case the plate heights of the microplates differ. In order to adjust a sharp imaging of the wells of the microplate on the chip of the CCD camera, an adjusting unit is advisably provided for vertical displacement of the entire optics and camera block. However, a complete autofocusing unit can also advantageously be provided.

The basic idea of the invention stems from the fact that for the enormous number of examinations of assays in an HTS regime that are required in biochemistry or pharmacology the increasing demand for flexibility in the dispensing devices and observation devices is frustrated because in order to use different microplates either the dispensing heads must be changed or an intermediate rinsing is required which permits multiple pipetting of the microplate with a smaller quantity of dispensing tips when the quantity of wells differs. Further, a measurement initiated immediately upon dispensing into the wells is a problem whenever dispensing is carried out in a plurality of steps per microplate. In this case, it is not possible to carry out large-area observation over all of the wells due to the required high detection sensitivity for luminescent radiation and the observation of individual wells impedes the continuation of the dispensing steps due to the required measuring time for progressive observation. According to the invention, these competing phenomena are reconciled through the use of at least one linear dispensing comb which has a symmetrical treelike structure and an even number of dispensing nozzles representing an integral divisor of the number of wells in one dimension of the microplate, is connected to a controllable pump for metering the amount of liquid to be dispensed (without immersion in the wells of the microplate) and is displaceable orthogonal to its longitudinal dimension in order to dispense successively in a preselected area. At least this preselected rectangular area is observed on the underside of the microplate opposite the dispensing unit with a very fast objective and possibly, in addition, by a CCD camera which is intensified by a light intensifier while dispensing is being carried out, so that the course of luminescence over time can be measured.

By means of the solution according to the invention, it is possible to dispense into a plurality of individual specimens in multi-specimen arrangements such as microplates and at the same time to observe the course of emitted luminescence over time, and, in so doing, to realize a high specimen throughput (HTS). The device according to the invention is characterized by great flexibility with respect to the measurement of different microplate types and microplate sizes and permits the use of a plurality of different dispensing substances on a microplate and different metering of dispensing substances in different columns of the microplate without substantially retarding the HTS process.

The invention will be described in more detail in the following with reference to embodiment examples.

DESCRIPTION OF THE PREFERRED EMBODIMENTS

Figure 1:
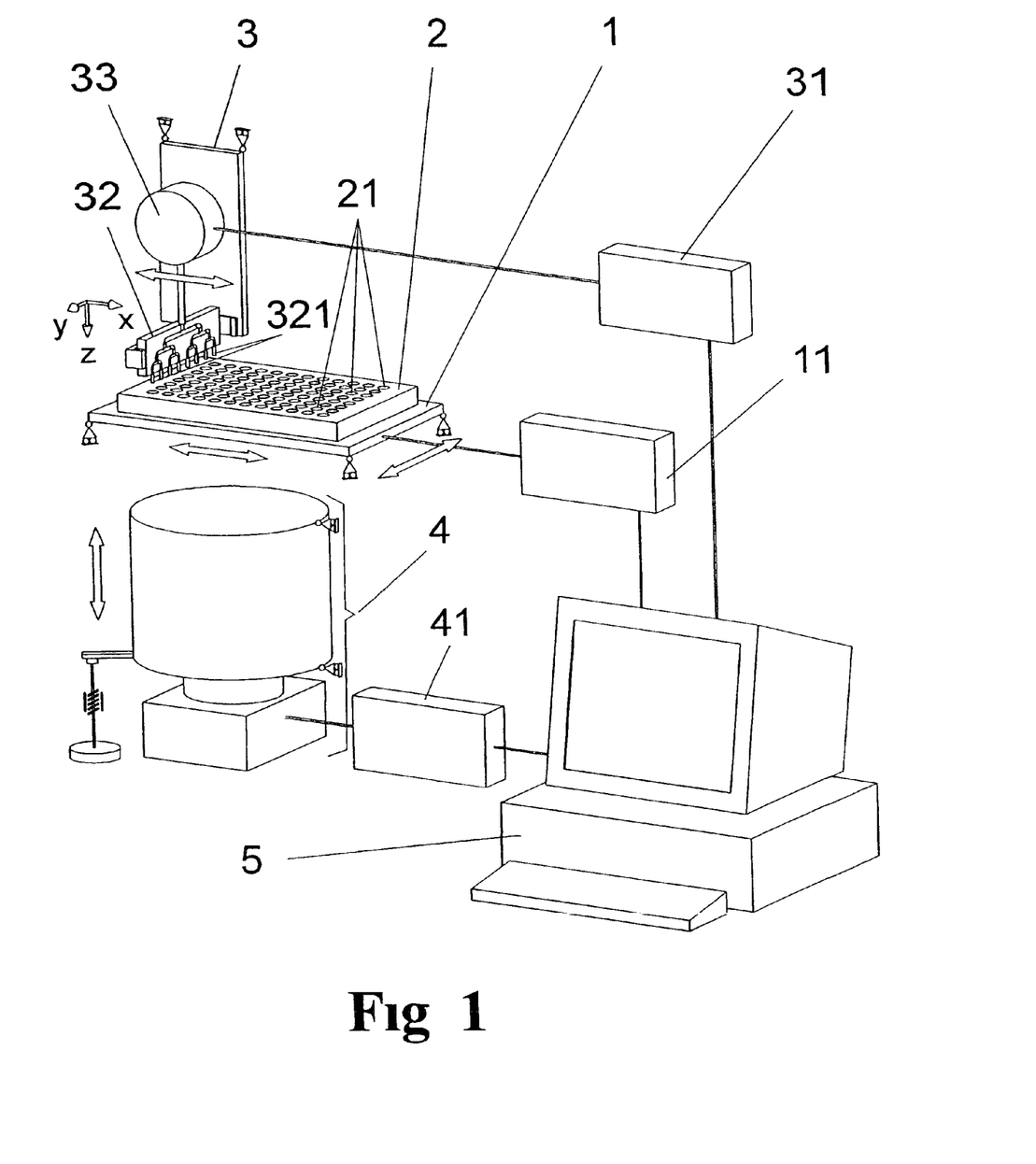
FIG. 1 shows a schematic view of the device according to the invention.

In its basic construction, the device according to the invention comprises—as can be seen from FIG. 1—a table system 1 with associated table control 11, a microplate (MP) 2 placed on the latter, a dispensing unit 3 with dispensing control 31, a CCD camera block 4 with camera control 41, and a controlling computer 5 which is preferably a PC for sequence control and coordination of dispensing, image recording, preparation, storage and output/display of the optical measurement data.

The table system 1 is an x-y table, although for special applications of the device according to the invention only one movement in y-direction is required for feeding the MP 2 into the device. The MP 2 has a plurality of wells 21 containing the specimens in which substances are to be dispensed and which are measured with respect to luminescence. The wells 21 are ordered in rows and columns in the MP 2 and are arranged in a fixed grid whose dimensions depend on the density (i.e., the quantity of wells 21) of the MP 2. Currently, primarily standardized 96-well, 384-well and 1536-well plates are used and can be processed, i.e., dispensed in and measured, in the same way in the device according to the invention without the required HTS regime being impaired by adapting the dispensing regime and measuring regime to the quantity of wells 21 of the MP 2. However, the invention can also easily be adapted to any other MP formats (192-well, 864-well, 2400-well, 3456-well or 6144-well MPs) because the quantity of wells per column and per row of any MP is always a multiple of 8 or 12 and consequently it is only necessary to adapt the nozzle spacing and/or nozzle quantity to the dispensing unit 3.

The addition of liquid is usually carried out inside the light-tight device (not shown) by means of a dispensing pump 33 with a connected dispensing comb 32 (as will also be described in detail with reference to FIG. 7). The nozzles 321 of the comb 32 fit exactly into the individual wells 21 of an MP 2.

The dispensing unit 3 arranged above the MP 2 in FIG. 1 has a specially designed dispensing comb 32 which has eight linearly arranged dispensing nozzles 321. The comb 32 has a symmetrical structure which is branched in a treelike manner and—as is indicated in FIG. 1 and known in principle from DE 199 11 456 A1—the supply channel coming from a pump 33 is branched symmetrically in pairs and correspondingly tapered after every branch, so that the same pressure and the same volume flow occur at all dispensing nozzles 321 when the pump 33 conveys a determined amount of dispensing liquid. The dispensing nozzles 321 dispense without contacting the liquids already present in the wells 21, i.e., there is no entrainment of specimens. The volumes delivered by the individual nozzles 321 are very constant because all of the nozzles 321 are subject to the same pressure and because the pump 33 works with a very accurate stepping motor. The equal, constant pressure is achieved by the internal symmetrical channel structure in the comb 32.

In contrast to conventional pipetting heads which dip into the wells of the MP and must be lowered in z-direction for this purpose, this special dispensing comb 32 dispenses (more precisely, sprays) the dispensing liquid in defined drops and the dispensing unit 3 is always left at the same height in the z-coordinate. However, the dispensing unit 3 is moved orthogonal to the longitudinal dimension of the comb 32 in x-direction relative to the MP 2 (i.e., normally relative to the row direction of the MP 2). This is carried out on the one hand to compensate for deficiency in the second dimension of the dispensing comb 32 but, on the other hand, above all to achieve a simultaneous luminescence measurement in the image field (visual field) detected by the CCD camera block 4 during the continuously progressing dispensing, which makes it possible to measure the course of luminescence starting with the dispensing for a determined time window (in the range of seconds up to some 10 s).

The device shown herein can process all known MP formats (e.g., MPs 2 with 96, 192, 384, 864, 1536, 2400, 3456, and 6144 wells 21), although only standard MPs with 96, 384 or 1536 wells will be discussed in the following.

In the standard MPs mentioned above, there are columns in y-direction with 8, 16 or 32 wells which intersect in x-direction with rows of 12, 24 or 48 wells. The greatest common divisor (8 or 12) of the number of wells 21 of the MP 2 in one of its two dimensions is selected as the quantity of nozzles 321 in the dispensing comb 32 in order to be able to use the device in its entirety with all of the standard MP sizes mentioned above. Because of the improved ability to control the pressure in a comb 32 with few nozzles 321, the direction of the comb 32 is preferably oriented in the shorter dimension of the MP 2 (in y-direction which usually lies in the supply direction=main forward feed direction of the MP 2).

However, when the comb 32 is outfitted with 12 nozzles 321, it can be oriented in an equivalent manner in x-direction and displaced in y-direction. Accordingly, the displacing direction of the dispensing unit 3 relative to the MP 2 can also be selected in a different way depending on the comb 32 that is used.

Figure 2:
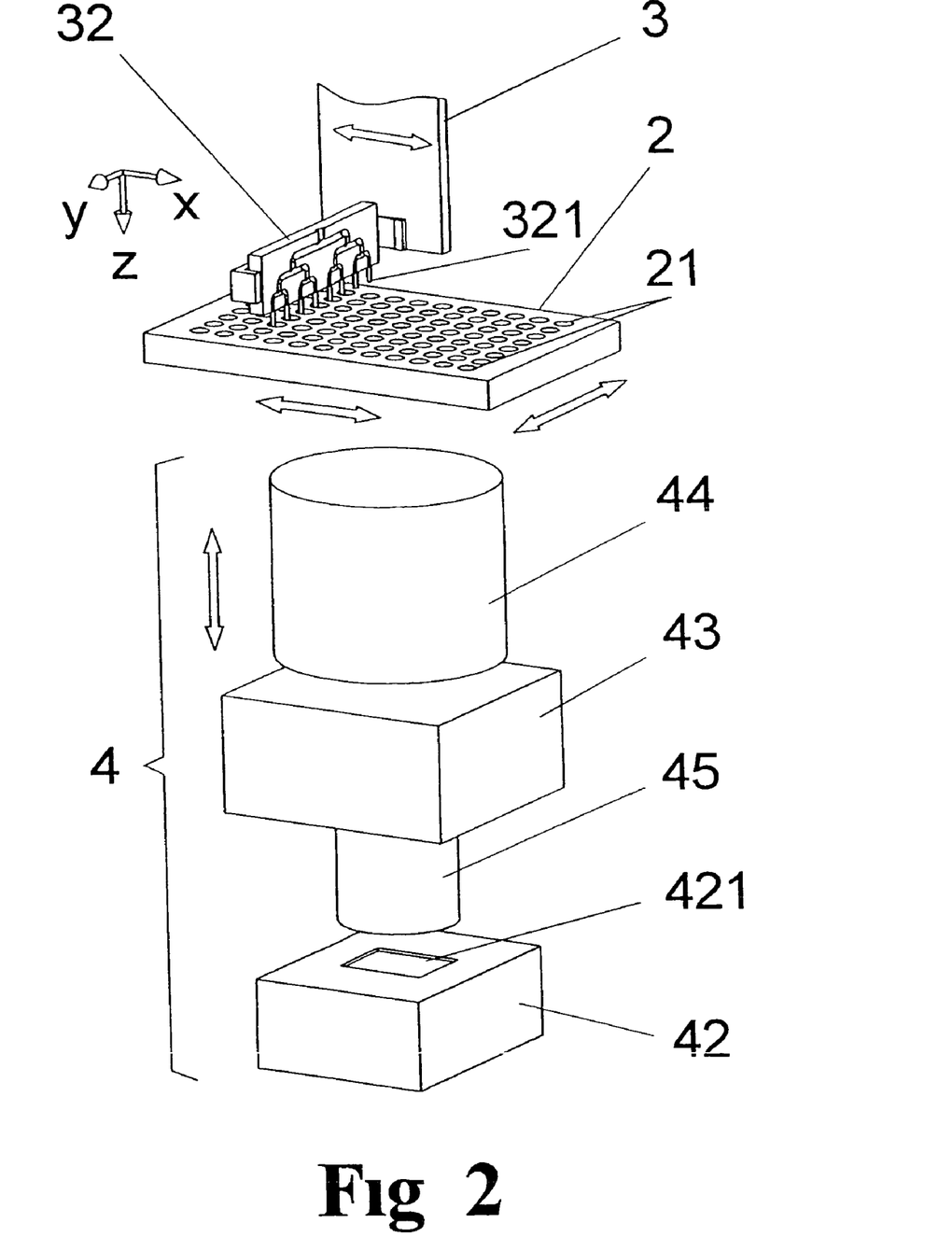
FIG. 2 shows a variant of the optical scanning system with a conventional fast objective.

When the quantity of dispensing nozzles 321 matches the quantity of wells 21 in one dimension of the MP 2, the dispensing process can be realized for the entire MP 2 in one motion as is indicated in FIG. 1 without limiting generality. For a case of this kind, FIG. 2 shows the construction of a CCD camera block 4 by which the MP 2 is observed completely in one frame by the CCD camera 42 (for example, when dispensing in a 96-well MP 2 with a dispensing comb 32 outfitted with eight nozzles 321). Since an MP 2 is to be provided with dispensing liquid at the same time that observation takes place, the camera block 4 is arranged under the MP 2, and the MP 2 must have a transparent bottom. The dispensing comb 32 is moved continuously in x-direction over the entire MP 2 during the image recording and dispenses liquid in the wells 21 of the MP 2 by column with eight simultaneous shots or salvos, i.e., with a uniformly metered and synchronous liquid delivery (as a jet) from all nozzles 321 of the comb 32. In so doing, the CCD camera 42 continuously takes pictures of the entire underside of the MP 2 and, synchronous with the start of the dispensing into the wells 21 (by columns), contacts associated observation windows in which the course of the luminescence triggered by the dispensed substance is detected over time and filed in sequence in the PC 5. The PC 5 has the master control function for synchronizing the dispensing in column direction and the ordered readout of the measured luminescence values. The dispensing unit 3 with the comb 32 is physically positioned over the very sensitive middle area of the visual field of the camera 42.

The twelve columns of a 96-well MP 2 are worked by a displacing process of the dispensing unit 3. For this purpose, a comb 32 is employed whose nozzles 321 have a spacing of 9 mm corresponding to the center distance of two wells 21 of a 96-well MP 2.

In an MP 2 with 384 wells, the x-y table 1 is moved in such a way that the first eight rows are initially filled (by drops) column by column with the dispensed substance by the continuous displacement of the comb 32. Subsequently, the MP 2 is displaced in y-direction by eight rows by means of the table system 1 in order to process the second row area. A comb 32 whose nozzles 321 have a spacing corresponding to the center distance (4.5 mm) of two wells 21 of a 384-well MP 2 is used for this purpose.

The use of a CCD camera 42 for measuring luminescent light is possible only because the CCD camera 42 is "intensified", i.e., it is outfitted with a very fast commercial objective 44 (e.g., Leica f#1, f=50 mm, with an object-side numerical aperture NA=0.08) and a residual light intensifier 43 (micro-channel plate or image intensifier similar to a night vision device) and has a normal video rate of 25 frames per second. Therefore, there is a complete imaging with 5.5× reduction of the MP 2 on the camera chip 421 by means of slightly reducing relay optics 45 which are arranged between residual light intensifier 43 and CCD camera 42. During the imaging, the luminescent light generated in the individual wells 21 is transferred from the underside of the MP 2 located in the object plane of the objective 44 to the residual light intensifier 43 comprising the fiber optic plate, electron optics and micro-channel plate (not shown individually). The fiber optic plate receives the luminescent light and directs it to the cathode of the electron optics. The electrons ejected from the latter are accelerated and imaged at 1:1 on a micro-channel plate which acts like a plurality of electron multipliers (PMT) and the electrons hit a phosphor screen on the output side of the micro-channel plate. Several hundred photons are generated per incident photon and are imaged on the camera chip 421 by relay optics 45.

Figure 3:
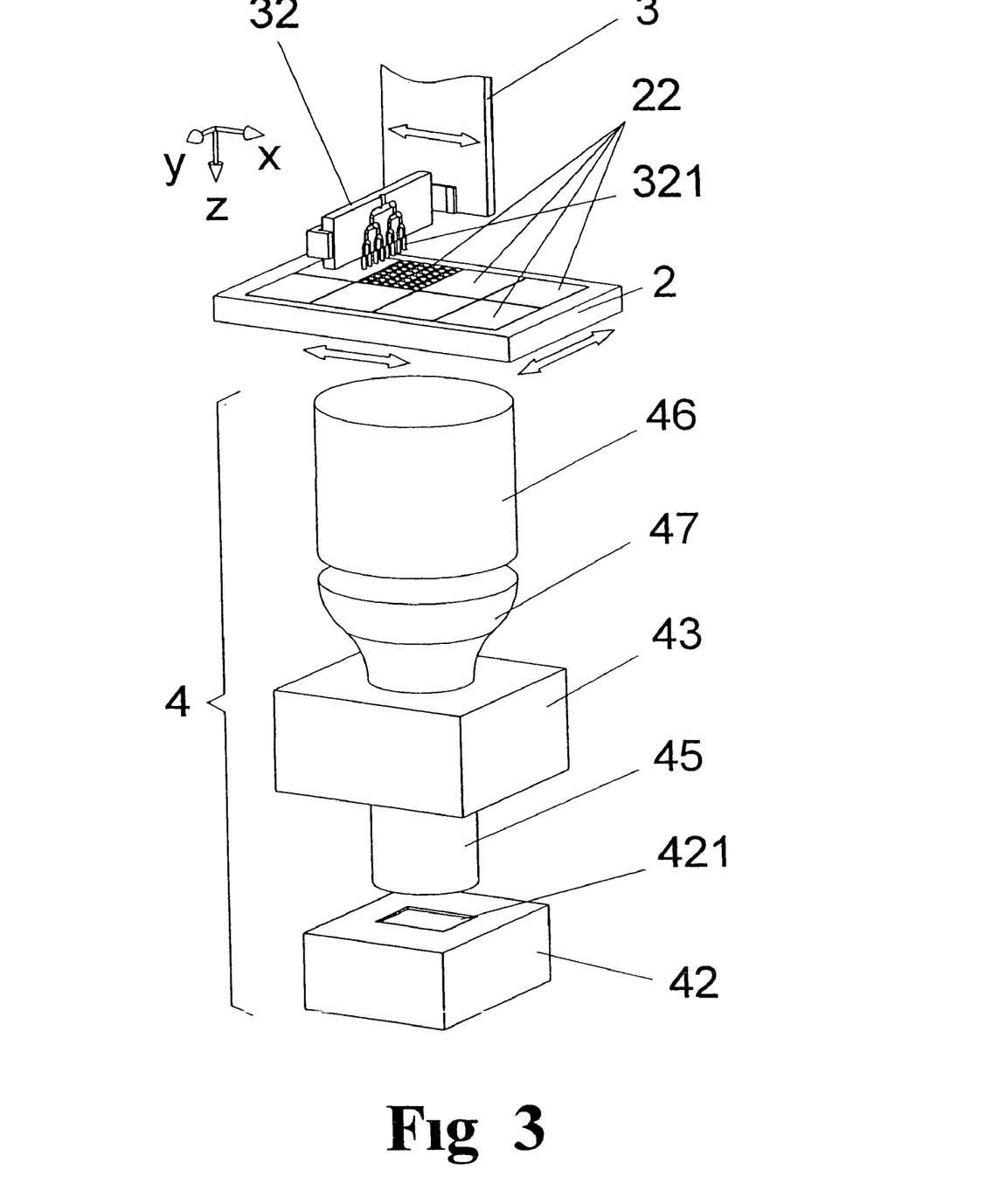
FIG. 3 shows a variant of the optical scanning system with a fast telecentric objective.

FIG. 3 shows a CCD camera 42 having an even greater light gathering power in a further modified camera block 4. This embodiment example is tailored to 384-well and 1536-well MPs 2 in particular because with increasing well density (and accordingly decreasing volume per well) a faster optical imaging is desirable and the greater quantity of wells 21 makes it necessary to scan by portions (at least in the row direction of the MP 2) because of the currently limited length of the dispensing combs 32 for dispensing by drops.

The requirements mentioned above are met by the use of a fast telecentric objective 46 combined with a subdivision of the MP 2 in a plurality of rectangular portions (hereinafter tiles) 22 of equal size.

The dispensing unit 3 is displaced only over the width d (only shown in FIG. 4) of a tile 22. The length c of the tile 22 matches the longitudinal dimension of the comb 32. After the dispensing unit 3 is moved over a tile 22 and after the measuring time for detecting the course of luminescence (for flash luminescence less than or equal to 20 seconds) elapses, the x-y table 1 (shown only in FIG. 1) moves the MP 2 placed upon it to a new position for dispensing in and measuring the next tile 22. The movement pattern of the table system 1 can be selected in any manner desired. In this example, the "intensified CCD camera" comprises the camera block 4 according to FIG. 3. Light is generated corresponding to the dispensing in the individual wells 21 of the tiles 22 of the traversed MP 2. The fast telecentric objective 46 (e.g., with a numerical aperture NA=0.45) generates an image of ⅛ of the MP 2 on a taper 47 which is optically connected to the input of the residual light intensifier 43 (already described in the previous example). A fiber optic plate receives the light with an aperture of NA≈0.9 and—as was described above—conveys it inside the residual light intensifier 43. The photon-multiplied image is imaged on the CCD camera 42 by relay optics 45. There is a total reduction by a factor of 6 of the visual field of ⅛ of the MP 2, so that the MP 2 is subdivided into eight tiles 22 of equal size for the above-mentioned telecentric objective 46 in order to carry out simultaneous dispensing and measurement of luminescence.

Figure 4:
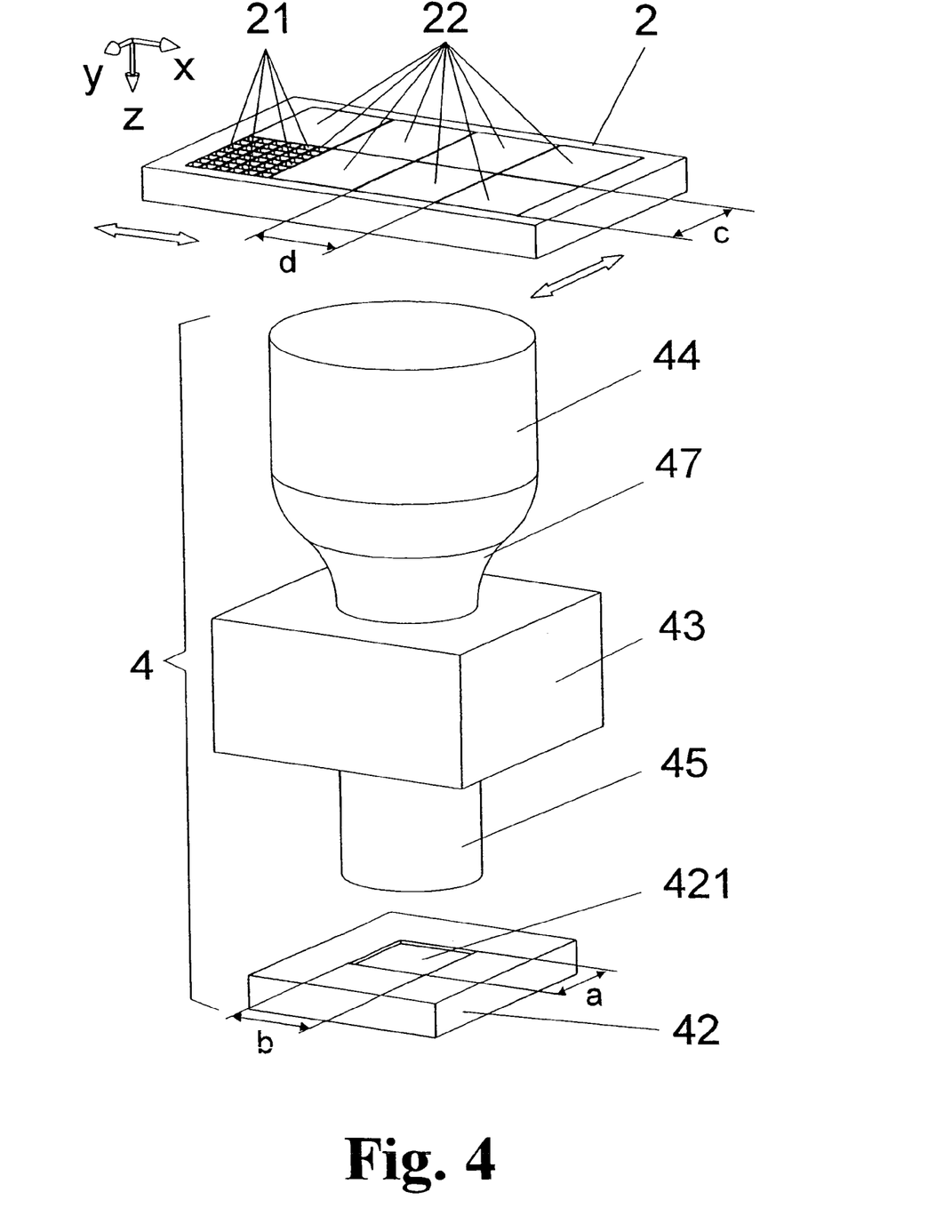
FIG. 4 shows a schematic view illustrating the adapting of the imaged portions of the microplate relative to the chip of the CCD camera with a telecentric objective.

FIG. 4 shows the arrangement in FIG. 3 again in a schematic manner to illustrate the adaptation of the visual field of the CCD camera 42 to the format of the tiles 22. The dimensions of the tiles 22 of equal size are indicated by c×d and the surface of the camera chip 421 is indicated by a×b. The following tile sizes (rows times columns) are imaged depending on the type of MP:

96-well: 4×3; 384-well: 8×6 1536-well: 16×12.

The 96-well MP 2 will not be discussed in detail because a comb 32 with only four nozzles 321 is used in this case, although it must be handled in exactly the same way as the combs 32 with eight nozzles 321 in the following examples.

The working of the larger MPs 2 is carried out in a manner analogous to that already described. With a 384-well MP 2, dispensing is carried out in the six columns of a tile 22 immediately one after the other, while the CCD camera 42 takes continuous images of this tile 22. The entire MP 2 is then offset (by the x-y table 1) and the visual field of the CCD camera 42 is therefore directed to the next tile 22 and dispensing is carried out in the next six columns.

Figure 5:
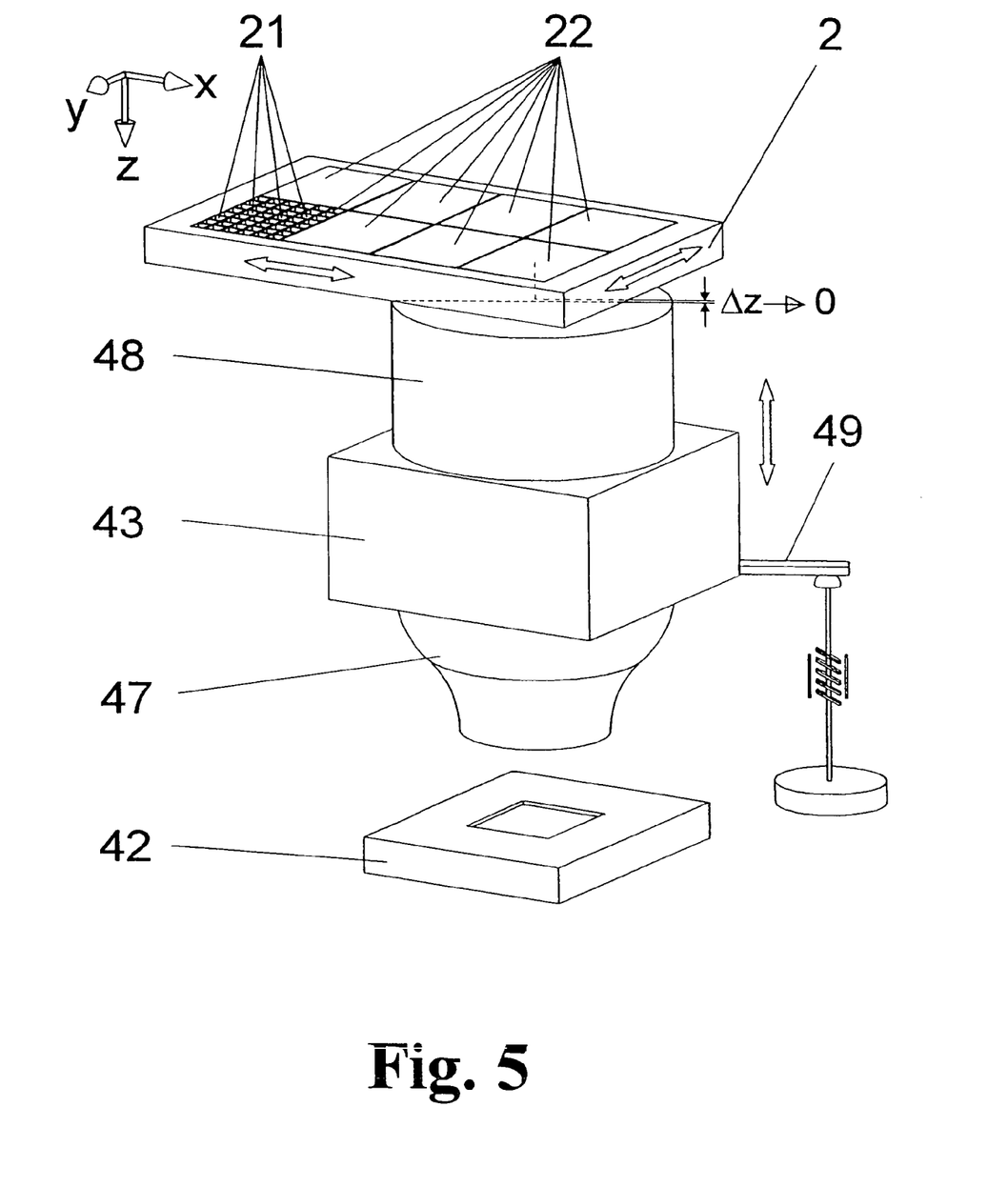
FIG. 5 shows a schematic view illustrating the adapting of the imaged portions of the microplate relative to the chip of the CCD camera with a fiber optic plate for optical imaging instead of an objective.

The procedure for dispensing and scanning provided in FIG. 5 is the same as in FIG. 4, except that the camera block 4 is realized in a different way optically and in this example comprises a parallel fiber optic plate 48 (with 1:1 imaging), a residual light intensifier 43, and a taper for reducing the imaging size. The difference consists in the need for contact of the fiber optic plate 48 with the bottom of the MP 2. This is because the fiber optic plate 48 has an aperture of almost 90° which necessitates contact with the MP 2. For this reason, an adjusting unit 49 is provided at the camera block 4 by means of which the optics are lowered when changing from one MP 2 to the next or when the table 1 is moved to reach the next tile 22. After the MP 2 is displaced, the camera block 4 comes into contact again with the MP 2. But the x-y table system 1 could also have a height adjustment or there could be a crank guide for lifting and lowering the MP 2 in the table 1.

Figure 6:
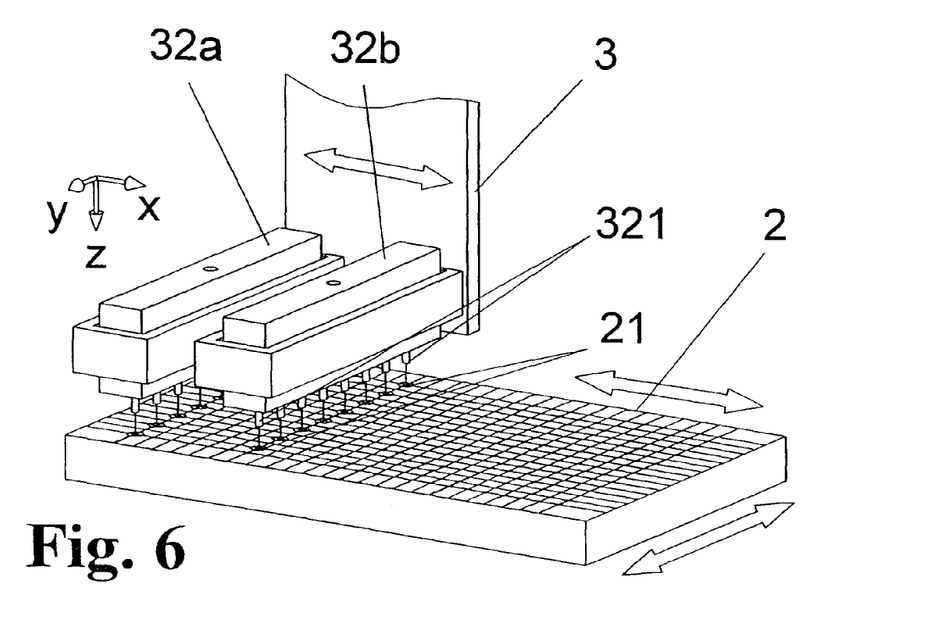
FIG. 6 shows an arrangement of the dispensing unit for the use of two offset dispensing combs for microplates having tighter grid dimensions than the nozzles of the dispensing comb.

For a 1536-well MP 2, FIG. 6 shows a variant arrangement of the invention in which a comb 32 with eight nozzles 321 (with a nozzle distance of 4.5 mm) can likewise be used. This example does not limit the possibility of using a comb 32 with sixteen dispensing nozzles 321 for a 1536-well MP 2, but rather should use a comb 32 with eight nozzles 321 (with a distance of 4.5 mm) as a type of standard.

The double-comb arrangement, shown in FIG. 6, in which there is a pump 33 in the dispensing unit 3 for comb 32*a* and 32*b* (shown only in FIG. 6) is used in this case. The combs 32*a* and 32*b* are arranged at the dispensing unit 3 so as to be offset by 2.25 mm (i.e., the distance between the wells of a 1536-well MP) in the direction of their nozzles 321. Due to the size of the comb body, there is also an offset by at least two wells 21 in the x-direction of the MP 2, but this can be corrected in a simple manner by a time offset of the start and end of dispensing with the combs 32*a* and 32*b* during continuous scanning of a tile by means of the CCD camera 42 and by means of filing the measured luminescence values in an ordered manner as a hypothetically offset (nested) opening and closing of scanning windows in accordance with the actual column assignment of the wells 21.

A first half of the MP 2 (or a tile 22 thereof) is initially displaced in the visual field of the CCD camera 42 during the scanning of the entire MP 2 with the method described above.

Two 8-fold combs 32*a* and 32*b* arranged at a fixed distance from one another in the x and y directions are advisably used. Every comb 32*a* and 32*b* has a fixed distance of 4.5 mm between the nozzles, so that dispensing can take place only in every second well 21. The two combs 32*a* and 32*b* move together over the MP 2 at a constant speed. Accordingly, different dispensing modes can be carried out:

a) Both combs 32*a* and 32*b* dispense the same liquid. The combs 32*a* and 32*b* must be activated and deactivated one after the other at the edges of the MP 2. This results in the advantage of a faster dispensing in the entire MP 2 or tile 22 thereof.

b) The two combs 32*a* and 32*b* dispense different liquids. In this case, the two combs 32*a* and 32*b* have the same y-position. Two dispensing substances whose combined action triggers the light reaction can be dispensed very quickly one after the other. However, dispensing is effected only in every second well 21 of the columns of the MP 2, so that the MP 2 must be offset by one well spacing in y-direction after all of the columns are worked. However, in an equivalent manner, another double-comb can also be arranged so as to be offset by 2.25 mm in parallel relative to the two first combs 32*a* and 32*b*, or there can be two combs 32*a* and 32*b* whose nozzles 321 have the same distance as the wells 21 on the MP 2.

Another variant of the dispensing principle described above when the dispensing unit 3 has only one comb 321 can easily be derived from FIG. 6 and can consequently be applied in an equivalent manner. In this case—in a manner very similar to the description with respect to FIG. 6—a 1536-well MP 2 is worked in that dispensing is initially carried out only in the odd-numbered rows of all columns of the MP 2 (from left to right in positive x-direction). Subsequently, the MP 2 is offset in y-direction by one well 21, i.e., by 2.25 mm (well spacing of a 1536-well MP), so that dispensing can then be carried out in the even-numbered rows of all columns. In this way, dispensing is carried out by drops in all sixteen wells 21 of every column. Subsequently, the x-y table 1 is displaced in a second row area and the same procedure is repeated for the second sixteen rows.

During the measurement of the 1536-well MP 2 by a telecentric objective 46 (according to FIG. 3 and FIG. 4), the individual tiles 22 are moved over the visual field of the camera 42 in the same way as was described above with an intermediate step of 2.25 mm in each instance. The eightfold comb 32 with a nozzle distance of 4.5 mm which is also used, according to the invention, for the 1536-well MP is first used in every tile 22 for the odd-numbered eight rows 1, 3, 5, . . . 15, since the well distance is 2.25 mm and the comb 32 therefore only reaches every second well, and when the MP 2 has been displaced in y-direction by 2.25 mm dispensing is carried out in the even-numbered rows 2, 4, 6, . . . 16 of the same tiles before the MP 2 is displaced for dispensing in and observation of the next tile 22.

Since the combs 32 are readily exchangeable without changing the pump 33, the device according to the invention can easily be adapted to any MP 2 under examination and to any dispensing situation. In this connection, the comb structures that are primarily selected are those in which the comb 32 need only be moved in x-direction when possible. This also applies to the 1536-well MP when using a comb 32 with correspondingly close distances between the nozzles 321 (2.25 mm).

Figure 7:
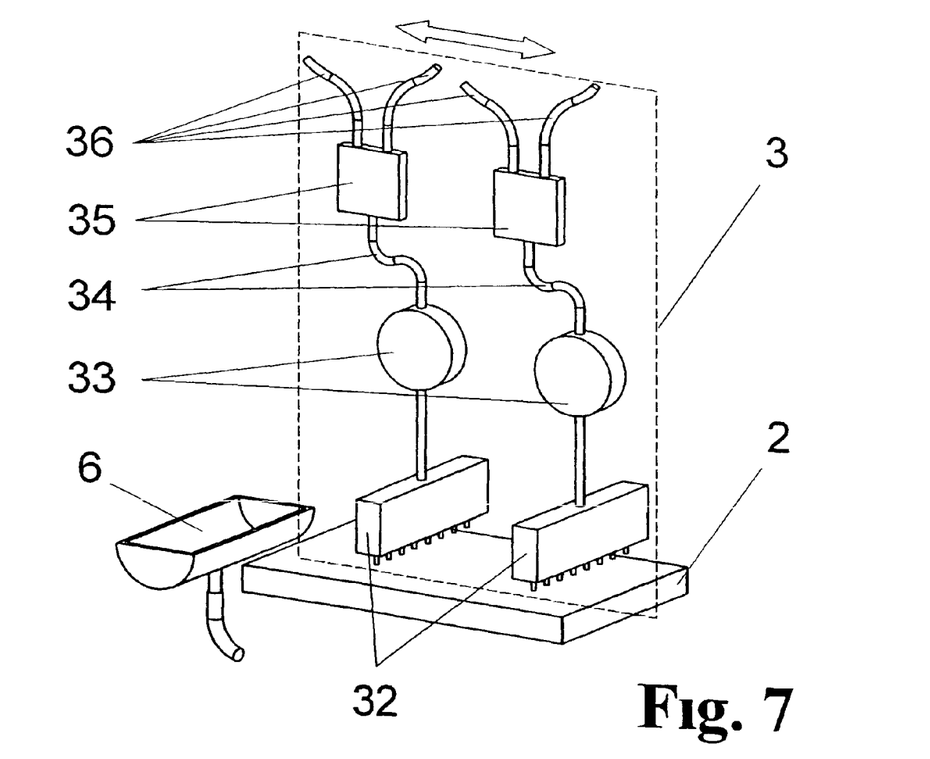
FIG. 7 shows a variant of the dispensing unit for a plurality of different dispensing liquids.

The device according to the invention achieves its special advantage in an arrangement according to FIG. 7.

The liquid handling which is integrated in this construction makes it possible for different dispensing liquids to be used on an MP 2. As is already known in principle in the prior art, this is carried out by means of two dispensing combs 32 which dispense in the same columns of wells 21 so as to be offset in time. In addition, however, there is also a possibility of switching combs 32 without the need for washing the combs 32. For this purpose, the different dispensing liquids are supplied via supply tubes 36 to a bidirectional valve 35 which communicates with the respective pump 33 of a comb 32 via connection tube 34. It is possible to choose between the dispensed substances at valve 35 by means of software. The pump 33 which is controlled by a stepping motor then conveys a defined but adjustable volume in a precise manner. The conveyed dispensing substance is injected into the dispensing comb 32 which distributes the volume uniformly to the (e.g., eight) nozzles 321. FIG. 7 shows two pumps 33 which are mechanically connected and move at a constant speed over the MP 2. This is indicated by the double arrow. As was described in the previous examples, movement of the MP 2 is also possible as illustrated by double arrows.

The cross section of the nozzles 321 is so small that the pressure that is applied briefly via the pumps 33 results in the preselected quantity of liquid being pushed out at equal pressures and in a neat separation of the drops or jets. The dispensing liquid has a high exit speed. The quantity of nozzles 321 is again fixed at eight. The pressure is built up by the pump 33 which is controlled by a stepping motor. Every comb 32 must have its own pump 33. The number of pumps 33 is limited to two in this example since most known biochemical light reactions require the delivery of at most two different dispensing liquids.

The pumping speed v must be optimized for a liquid to be dispensed by drops. A liquid with a higher viscosity has different separation behavior than, e.g., distilled water. This parameter (pumping speed v) is controlled by software. In the event that a drop does not detach itself, it would drip in an uncontrolled manner into the next well 21 during the next dispensing process or would drop on the intermediate space between wells in the MP 2. This must be avoided at all costs. Therefore, the pumping speed can be adjusted corresponding to the viscosity of the dispensing liquid.

The controllable valves 35 and the volume adjustment are not time-critical, since constant volumes are required and selected for an assay in HTS. Therefore, adjustment can also be carried out manually. Nevertheless, volume adjustment by software is provided. This increases the flexibility of the device according to the invention so that complex applications can also be carried out in the future in case drops are to be dispensed in an MP 2 multiple times with different dispensing liquids and dispensing volumes.

It is possible to choose between at least two different dispensing substances with the valve 35 per pump 33. The valve 35 has the function of switching between different supply tubes 36.

When switching between the dispensing liquids, however, the previously used liquid must be removed. This is generally carried out after working an entire MP 2 because the comb 32 and the connection tubes 34 must first be emptied into a waste trough 6. An automatic software-controlled version can also be provided for this purpose. In this way, more complex assays can be worked and the flexibility of the device is therefore increased.

Since the volume in the pump 33, in the comb 32 and in the connection tubes 34 is very small (only 100 to 200 μl compared to a filling amount of several milliliters in a conventional pipetting head for a 384-well MP), the solution according to the invention is substantially more economical with respect to the consumption of dispensing reagents. Further, no washing is required when changing (ejection of the first reagent) and consequently only a brief interruption of the dispensing and measuring is required. For this purpose, as is shown schematically in FIG. 7, a waste trough 6 is arranged parallel to the MP 2 at the end of the displacing area of the dispensing comb 32 as a narrow collection vessel, wherein the residual liquid from the last dispensing liquid used is ejected from the comb 32, pump 33 and connection tube 34 in that the new dispensing liquid is used substantially for displacement but also for rinsing.

Figure 8:
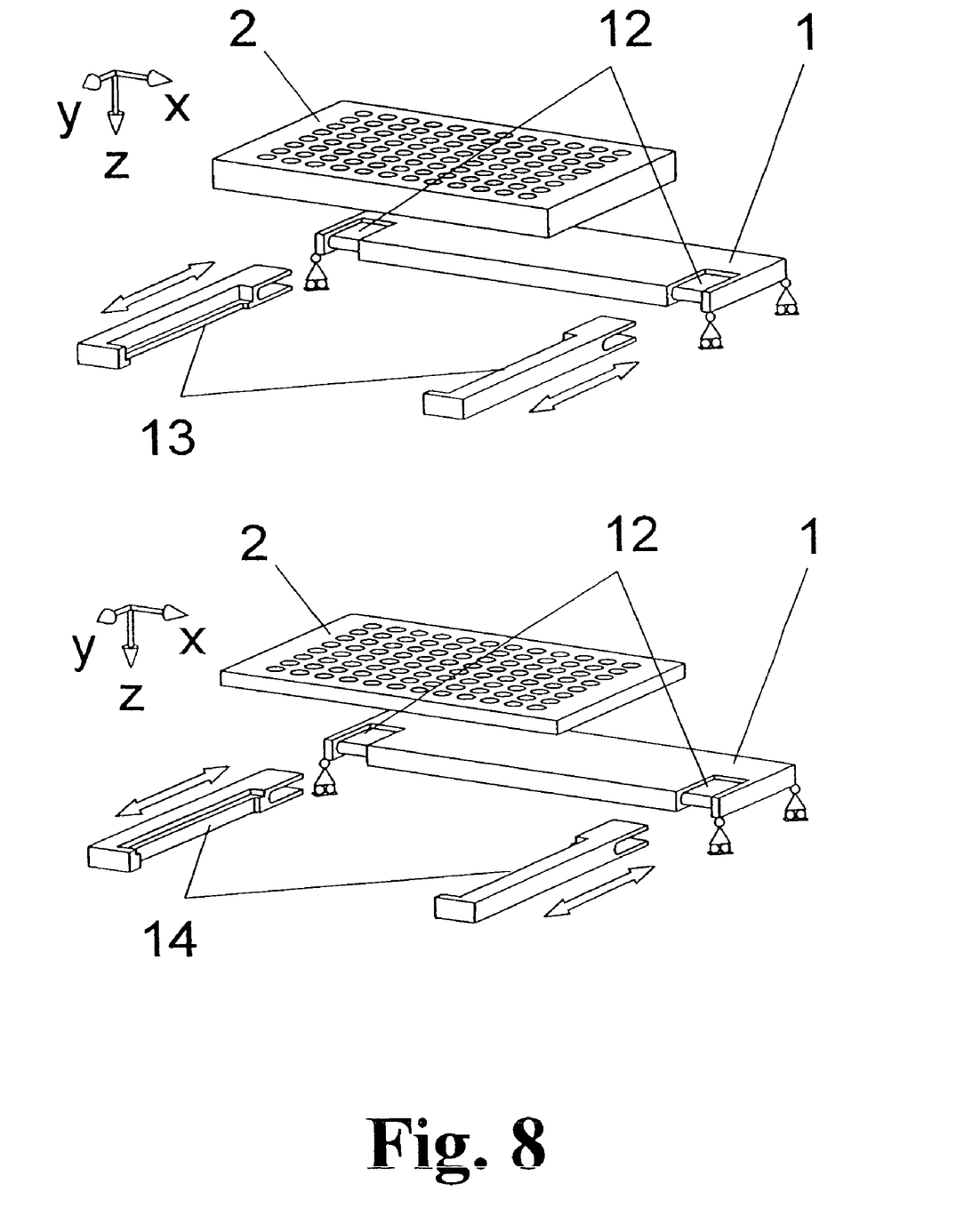
FIG. 8 shows a schematic view of different MP adapters for adapting to different thicknesses of the bottoms of the microplates.

There are different commercially available MP formats having virtually identical outer dimensions but different heights of the transparent bottoms, depending on the different types of MP. Consequently, the optics and the dispensing comb 32 must be adjustable with respect to height. Therefore, it is provided that the upper edge of the MP 2 is always at the same height so that the dispensing comb 32 need not be adjusted in height. For this purpose, the x-y table 1 has adapter holders 12 as is shown in FIG. 8 and is outfitted with exchangeable MP adapters 13 or 14 (depending on the height of the base of the MP 2 that is used), so that only the optics need to be adapted to the respective height. The quantity of adapters 13 or 14 to be exchanged is determined by the quantity of MPs 2 to be processed. Only two different pairs of adapters 13 and 14 are shown as exchangeable in FIG. 8; flatter MP adapters 13 are provided for the thicker MP 2 (upper part of the drawing) and higher adapters 14 are provided for the thinner MP bottoms.

In order to maintain the aspect ratio, the entire camera block 4 is vertically adjustable in the direction of the MP 2 by means of an adjusting drive 49 containing fine-adjustment drive guides and precision guides (shown only in FIG. 1 and FIG. 5). However, an autofocus system can also be used.

Further, the intensified CCD camera 42 has a dome-shaped sensitivity distribution with a maximum in the center and a corresponding edge drop-off. Therefore, it is advisable to carry out a calibration in order to achieve a homogeneous sensitivity for the entire visual field of the CCD camera 42 by means of electronic correction.

The dispensing comb 32 moves at constant speed over the visual field of the camera 42. The time interval between two successive dispensing steps can easily be determined from the known data—distance between two columns of an MP 2, constant traveling speed of the comb 32, and defined parameterized observation period of the camera 42—i.e., the opening and closing of the observation time window for every column in which dispensing is carried out is calculated by means of software. The signals of every well 21 are integrated in the time window. The window shifts, so to speak, with the dispensing comb 32 over the MP 2. The kinetics of all of the wells 21 can be shown in a scaled manner one over the other in spite of the time offset. The user receives the impression that the reagents are added simultaneously in all of the wells 21 of a tile 22 or of an MP 2 under observation.

The volume to be dispensed is likewise adjustable by software by corresponding control of a stepping motor in the pump or pumps 33 of the dispensing unit 3.

An advantageous flexibility results from the fact that the dispensing comb 32 preferably has eight nozzles which are oriented linearly in the column direction of the MP 2 and which are an integral divisor of the quantity of the wells 21 of the MP 2. Dispensing can be carried out in smaller areas of the MP 2 (e.g., individual columns or possibly also only portions thereof) for comparison measurements with different volumes of dispensing substance—even null volumes (no addition). Further, individual columns can also be selected for dispensing by software, which again increases flexibility and is not possible with currently available pipetting devices.

The volume that can be dispensed can also be varied in any way in that a determined quantity of identical added amounts (shots) are added by drops or shots per well 21. This has the advantage of a uniform mixing of liquids over the width of a well 21 (particularly in case of highly viscous specimen liquids and/or dispensing liquids). Further, repeated addition of constant quantities of liquid is advantageous in that amounts larger than the usual maximum volumes can be dispensed or a multiple of a "usual" added amount, for example, can be dispensed in different columns of the MP 2. In this regard, the adjusted volume always remains constant and the errors in volume adjustment are reduced. Commercial multiple pipetters (e.g., Hamamatsu) are not as flexible with respect to volume adjustment because the dispensing volume, once it is set, is delivered uniformly over all of the wells of the entire MP.

In a device according to the invention, no vertical movement mechanism is required for the dispensing head and dispensing can be carried out continuously without entrainment of specimens due to the drop technique that is used. Dispensing is also carried out over a plurality of MPs 2 without interim washing and the washing station that is normally required for cleaning the tips is omitted because there is no immersion in the wells 21 of the MP 2. Assays requiring the addition of two liquids directly one after the other for initiating light reactions can be measured without restrictions because the MP is not displaced relative to the visual field of the camera during the continuous dispensing in successive columns of the MP, so that a complete and continuous observation of kinetics is possible. Contactless dispensing is essentially superior to immersion pipetting due to the specimen purity that can be achieved, for reasons of cost due to the smaller quantities of dispensing liquid that are required, and because of the greater flexibility in changing the type and volume of dispensing substances.

An apparently longer dispensing period with only eight nozzles compared to the complete pipetting of all wells 21 of an MP 2 can be disproved by the following compensating effects.

a) The entire measuring period for flash luminescence is about 20 seconds. The constant speed of the comb over the MP requires about one more time period of this length, so that the entire dwell time of the MP in the instrument is doubled at most.

b) Since there is no longer a rinsing period or tip changing period, the next plate can be measured immediately (without additional intermediate steps).

c) When a plurality of different liquids must be added, a corresponding number of combs can be controlled in the device by a pump, so that they can dispense one after the other at a constant interval, while the camera can observe every addition (i.e., the camera can measure the course of luminescence).

Figure 9:
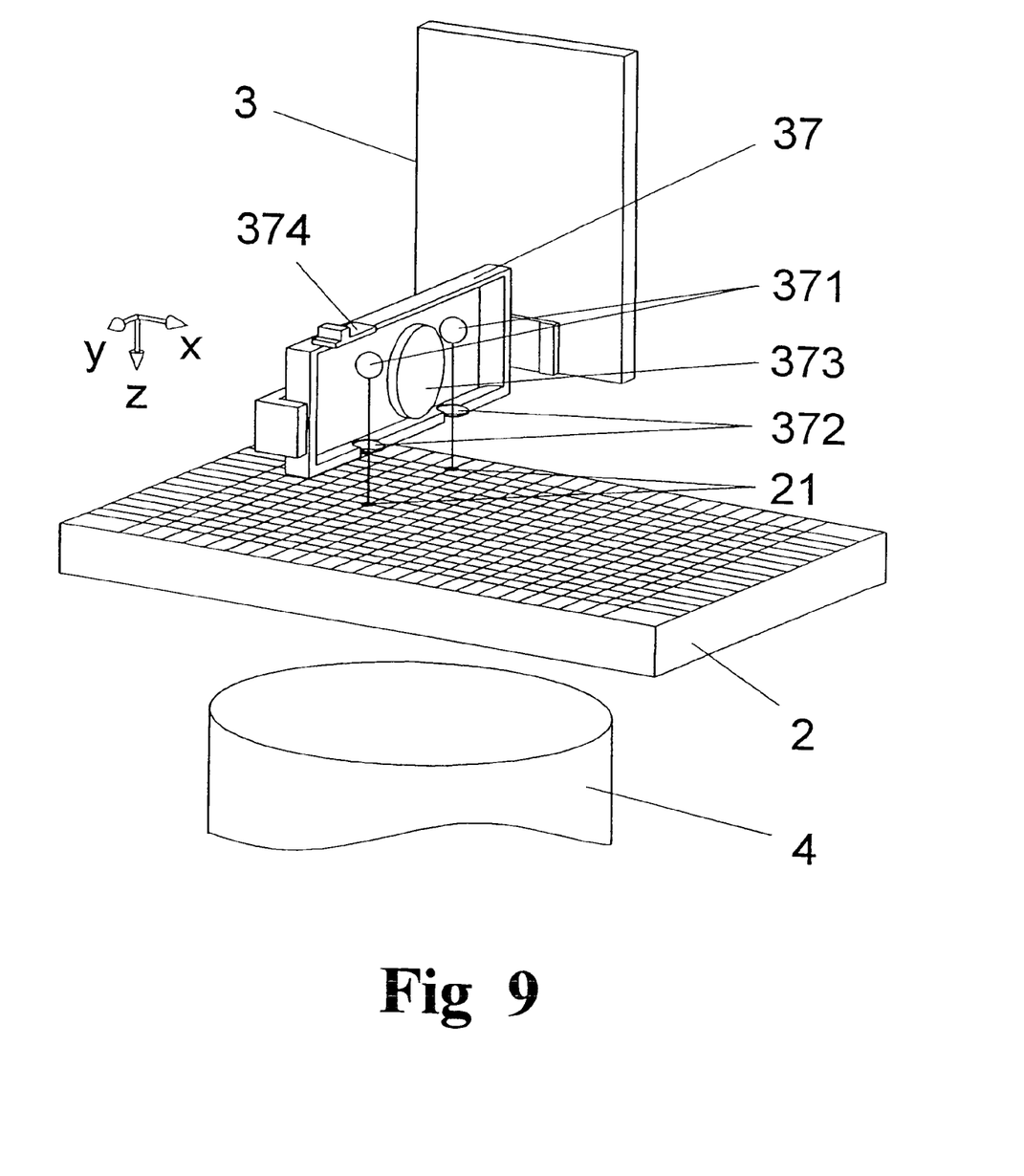
FIG. 9 shows a schematic view of a positioning device for aligning the dispensing unit relative to the table system.

An exact matching of the movement mechanism and the dispensing control 31 of the dispensing unit 3 is required in order to change as desired between different microplates 2. An adjusting comb 37 which takes the place of the dispensing combs 32 which would otherwise be used is used for these adjustments. An adjusting comb 37 of this kind is shown in FIG. 9. The adjusting comb 37 contains at least two light sources 371 and associated focusing optics 372 which illuminate the wells 21 corresponding to the grid of the MP 2. The light sources 371 are fed by a voltage source 373 (e.g., a battery or a round storage cell) which is operated by an external switch 374. The dispensing unit 3 and possibly also the table system are now moved in order to determine the state of the central position of the light spot of the focused light sources 371 under the MP 2 by means of the CCD camera block 4 and to generate corresponding control signals.

Other constructions of the device according to the invention described above are possible without departing from the framework of this invention. The examples described above were based on a dispensing unit 3 with a dispensing comb 32 having a fixed quantity of dispensing nozzles 321 which is the greatest common divisor of the quantity of wells 21 in one of the dimensions of conventional MPs 2. However, special constructions such as a double-comb arranged in an offset manner or a comb with 16 of the 32 nozzles lie within the framework of the invention. In particular, any multiple arrangements of rigidly coupled combs 32 which permit a complete dispensing in a whole column or row of an MP 2 are to be understood as also clearly falling within the teaching according to the invention insofar as this can be integrated in corresponding scanning windows of an image scanning of the MP 2 without inventive activity. The division of the MP 2 into a determined quantity of measurement portions (tiles 22) is exclusively subordinated to the fast optical system of the camera block 4 that is used and is in no way limited to eight.

The disclosed possibility of using a dispensing unit 3 with two dispensing combs 32 and two valves 35 for switching between four different dispensing substances is likewise purely arbitrary and can be converted at any time to any other dispensing requirements without inventive activity.

In addition to the fast, high-resolution arrangement disclosed herein in which the MP 2 is divided into eight observation portions (tiles), the invention also includes, of course, any other division of the MP 2, for example, into four or two tiles. All of the examples described above in which the MP 2 is divided into tiles can also be applied to the entire MP 2 with other suitable dimensioning of the dispensing device 3 and camera block 4.

While the foregoing description and drawings represent the present invention, it will be obvious to those skilled in the art that various changes may be made therein without departing from the true spirit and scope of the present invention.

| Reference Numbers | |
|---|---|
| 1 | table system |
| 11 | table control |
| 12 | adapter holder |
| 13 | flat MP adapter |
| 14 | high MP adapter |
| 2 | microplate (MP) |
| 21 | well |
| 22 | tile (portion of the MP) |
| 3 | dispensing unit |
| 31 | dispensing control |
| 32 | comb |
| 32a, 32b | first and second comb |
| 321 | nozzles |
| 33 | pump |
| 34 | connection tube |
| 35 | valve |
| 36 | supply tube |
| 37 | adjusting comb |
| 371 | light sources |
| 372 | focusing optics |
| 373 | voltage source |
| 374 | switch |
| 4 | camera block |
| 41 | camera control |
| 42 | CCD camera |
| 43 | residual light intensifier |
| 44 | fast objective |
| 45 | relay optics |
| 46 | telecentric objective |
| 47 | taper |
| 48 | fiber optic plate |
| 49 | adjusting unit |

| -continued | |
|---|---|
| Reference Numbers | |
| 5 | computer (PC) |
| 6 | waste trough |

What is claimed is:

1. An arrangement for dispensing and observing the luminescence of individual specimens in multi-specimen arrangements with high specimen throughput, particularly for the examination of biological, chemical or cytobiological assays comprising:

a microplate with a plurality of wells having transparent bottoms for observation of the luminescence and being arranged in rows and columns;

a dispensing unit with a fixed quantity of dispensing nozzles which is arranged over the microplate, wherein said quantity of dispensing nozzles of the dispensing unit being arranged in at least one linear dispensing comb with a number of dispensing nozzles representing an integral divisor of the number of wells along one dimension of the microplate and said at least one dispensing comb being displaceable orthogonal to its longitudinal dimension in order to progressively dispense into successively arranged columns or rows of wells of the microplate;

a table system for moving the microplate and the dispensing unit relative to one another;

an optical system by which the luminescent light that is excited in the wells of the microplate due to the dispensing is transferred to an imaging camera for observation of a large-area rectangular field of the microplate, wherein said large-area rectangular field is defined by the linear dimension of said at least one linear dispensing comb due to said number of nozzles of the comb in relation to the well pitch in one dimension of the microplate and, in the other dimension, by at least one microplate column;

and said imaging camera for receiving an image of said large-area rectangular field provided by said imaging optical system the imaging camera and said optical system provided in a camera block being directed to the underside of the microplate across from the dispensing unit, the imaging camera being a CCD camera for repeatedly receiving and storing a plurality of images over time, each image including all wells of the large-area rectangular field of the microplate, so that a course of luminescence over time for each individual specimen in all wells of the large-area rectangular field is measurable while simultaneously ongoing dispensing occurs successively column by column;

said above-mentioned components being located in a light-tight housing.

2. The arrangement according to claim 1, wherein the quantity of said dispensing nozzles corresponds to the quantity of wells in the columns of the microplate, so that the comb is displaced continuously exclusively orthogonal to its longitudinal dimension.

3. The arrangement according to claim 1, wherein the quantity of said dispensing nozzles is less than the quantity of wells of the columns of the microplate, wherein the quantity of wells in the columns of the microplate is an integral multiple of the quantity of said dispensing nozzles, and after the column-wise displacement of the dispensing comb in x-direction the microplate is displaceable in y-direction by a number of row spaces equal to the quantity of said dispensing nozzles in order to repeat the displacement of the dispensing comb in x-direction.

4. The arrangement according to claim 1, wherein the dispensing unit has a plurality of dispensing combs which are arranged parallel to one another, rigidly coupled with one another and displaceable over the surface of the microplate observed by the imaging camera.

5. The arrangement according to claim 4, wherein the dispensing combs are provided for successively dispensing different substances in the same wells of the microplate.

6. The arrangement according to claim 5, wherein the dispensing unit has, in addition, a controllable valve for each dispensing comb for switching between different dispensing substances, and the valves are arranged in front of the pump of every comb.

7. The arrangement according to claim 6, wherein a waste trough is provided next to the microplate in the displacement area of the dispensing comb for taking the dispensing substance, the waste trough being oriented parallel to the longitudinal dimension of the comb in order to expel the previously used dispensing substance still remaining in the comb, pump and connection tubes up to the valve in that it is displaced by a new substance.

8. The arrangement according to claim 4, wherein the dispensing combs are provided for successively dispensing the same substance in different wells of the microplate.

9. The arrangement according to claim 3, wherein said dispensing nozzles have twice the distance of the wells of the microp late, wherein dispensing is carried out only in the odd-numbered wells of the columns of the microplate in a first step and dispensing is carried out only in the even-numbered wells of the columns of the microplate in a second step.

10. The arrangement according to claim 9, wherein said at least one dispensing comb includes two dispensing combs arranged so as to be offset parallel to one another by half of the distance between the nozzles.

11. The arrangement according to claim 9, wherein said at least one dispensing comb is displaceable along its longitudinal dimension relative to the microplate by half of the distance between the nozzles of the comb.

12. The arrangement according to claim 11, wherein the relative displacement of the dispensing comb by half of the nozzle distance is provided by displacing the microplate in the y-direction between two different positions by the table system.

13. The arrangement according to claim 11, wherein the relative displacement of the dispensing comb by half of the nozzle distance is provided by displacing the dispensing unit in y-direction between two different positions.

14. The arrangement according to claim 1, wherein the optical system of the camera block has a fast objective, an electron-optical light intensifier, and reducing relay optics.

15. The arrangement according to claim 14, wherein the chip of the imaging camera is cooled.

16. The arrangement according to claim 14, wherein a commercial objective which images the microplate completely on the chip of the imaging camera is provided as the fast objective of the optical system.

17. The arrangement according to claim 14, wherein a telecentric objective with a high numerical aperture is provided as the fast objective of the optical system by which a rectangular portion of the microplate can be imaged on the chip of the imaging camera, wherein the dispensing unit is arranged above the visual field of the imaging camera that is defined in this way and its displacing area is adapted to the available visual field of the imaging camera.

18. The arrangement according to claim 17, wherein the microplate is divided into eight rectangular portions of equal size which can be introduced one after the other into the visual field of the imaging camera continuously and without overlapping by the table system, wherein the longer edge of the chip of the imaging camera is oriented in the direction of the short side of the microplate in order to compensate extensively for the side ratios of the chip and microplate and in order to make use of the whole visual field of the imaging camera.

19. The arrangement according to claim 1, wherein in order to adapt to different types of microplates an adapter holder is provided for fastening microplate holders to the table system in order to ensure a constant height of the upper surface of the microplate in case of different thicknesses of the microplates.

20. The arrangement according to claim 19, wherein an adjusting unit is provided for vertical displacement of the entire optics camera block in order to adjust sharp imaging on the chip of the imaging camera.

21. The arrangement according to claim 19, wherein an additional autofocusing unit is provided for adjusting sharp imaging on the chip of the imaging camera.

22. The arrangement according to claim 3, wherein said large-area rectangular field of observation successively covers at least half of the microplate surface.

23. The arrangement according to claim 3, wherein said large-area rectangular field of observation successively covers at least a quarter of the microplate surface.

24. The arrangement according to claim 3, wherein said large-area rectangular field of observation successively covers at least a sixth of the microplate surface.

25. The arrangement according to claim 3, wherein said large-area rectangular field of observation successively covers at least an eighth of the microplate surface.

* * * * *